United States Patent [19]

Detwiler et al.

[11] Patent Number: 4,788,153

[45] Date of Patent: Nov. 29, 1988

[54] METHOD FOR THE DETERMINATION OF BILIRUBIN AND AN ELEMENT USEFUL THEREIN

[75] Inventors: Richard L. Detwiler; David M. Taylor, both of Rochester, N.Y.

[73] Assignee: Eastman Kodak Company, Rochester, N.Y.

[21] Appl. No.: 106,759

[22] Filed: Oct. 8, 1987

Related U.S. Application Data

[63] Continuation-in-part of Ser. No. 918,241, Oct. 14, 1986, abandoned.

[51] Int. Cl.$^4$ .................... G01N 21/75; G01N 33/72
[52] U.S. Cl. ........................................ 436/97; 422/56; 422/57; 436/170
[58] Field of Search .................. 422/56–58; 436/97, 170

[56] References Cited

U.S. PATENT DOCUMENTS

| 4,069,016 | 1/1978 | Wu ........................... 23/230 B |
| 4,069,017 | 1/1978 | Wu et al. ................. 23/230 B |
| 4,311,665 | 1/1982 | Wu ............................... 422/56 |
| 4,338,095 | 7/1982 | Wu ........................... 23/230 B |
| 4,412,005 | 10/1983 | Wu ............................... 436/97 |
| 4,548,905 | 10/1985 | Wu ............................... 436/97 |

FOREIGN PATENT DOCUMENTS 59-230160 6/1983 Japan.
2085581 4/1982 United Kingdom.

*Primary Examiner*—Barry S. Richman
*Assistant Examiner*—Robert J. Hill, Jr.
*Attorney, Agent, or Firm*—J. Lanny Tucker

[57] ABSTRACT

A colorimetric assay for the determination of conjugated, unconjugated or total bilirubin in biological fluids can be carried out with an improved analytical element. This element comprises a support having thereon a substantially gelatin-free mordant layer comprising a positively-charged interactive mordant having at least one binding site for bilirubin, a radiation-blocking layer, and a porous spreading layer. This element does not contain any colorimetric or fluorometric interactive compositions for bilirubin other than the mordant.

13 Claims, No Drawings

METHOD FOR THE DETERMINATION OF BILIRUBIN AND AN ELEMENT USEFUL THEREIN

RELATED APPLICATION

This application is a continuation-in-part application of U.S. Ser. No. 918,241, filed Oct. 14, 1986, now abandoned.

FIELD OF THE INVENTION

This invention relates to a colorimetric assay for total, conjugated or unconjugated bilirubin in clinical chemistry. It also relates to a dry analytical element useful in this assay.

BACKGROUND OF THE INVENTION

Bilirubin is a degradation product of hemoglobin. In a healthy individual, bilirubin released from aged or damaged red blood cells in the body is excreted or degraded into other derivatives. In some cases, however, an excessive amount of bilirubin occurs within the body through overproduction of bilirubin as in the case of excessive hemolysis or liver failure. Invariably, the result of an excessive amount of bilirubin within the human body is jaundice which is characterized by markedly increased levels of bilirubin in serum. There is increasing evidence that excessive amounts of bilirubin in the blood can lead to an undesirable increase in bilirubin concentration within the body cells which interferes with various cellular processes. The clinical diagnostic significance of bilirubin determination, then, in tests for liver and other related organ functions, is apparent.

In human body fluids such as bile and serum, bilirubin exists in several different forms, these forms commonly being referred to in the art as conjugated bilirubin ($B_c$, both mono- and diconjugateed forms), unconjugated bilirubin ($B_u$, also known as indirect bilirubin) and delta bilirubin (also known as biliprotein). The total bilirubin content $B_T$ represents the sum of all forms of bilirubin.

A variety of colorimetric assays for bilirubin are known. At one time, the most widely used assay procedure was the diazo method which employs a coupling reaction of bilirubin with a diazonium salt to form a detectable pigment. This method has its disadvantages, and many variations and improvements have been developed over the years.

Other types of assays involve the direct measurement of bilirubin which is a yellow pigment. However, this technique is susceptible to spectral interference from hemoglobin and other components of the fluid sample. It also suffers from interference from protein materials, such as albumin, to which bilirubin can bind thereby producing a shift in absorption intensity and peak wavelength.

A significant advance in the art is described and claimed in U.S. Pat. No. 4,069,017 (issued Jan. 17, 1978 to Wu et al). The assay for bilirubin described therein is carried out with a dry multilayer analytical element containing an interactive mordant in a reagent layer which binds to bilirubin thereby producing a detectable product. No other interactive composition is used in the assay. The element also comprises a porous spreading layer and a radiation-blocking layer. The interactive mordant is dispersed in a binder material, such as gelatin or its derivatives, poly(vinyl alcohol), poly(vinyl pyrrolidone) and acrylamide polymers, that is homopolymers of acrylamides (See Column 15, lines 7-39). The Examples (Column 23) in this patent teach the use of gelatin as the matrix material. Indeed, such an analytical element for the determination of bilirubin containing gelatin as the binder material has been sold for a number of years.

Another advance in the art is described in U.S. Pat. No. 4,338,095 (issued July 6, 1982 to Wu) which relates to a method for selective determination of conjugated and unconjugated bilirubin. The assay is carried out with an element similar to that described in U.S. Pat. No. 4,069,017, and contains an interactive mordant for the bilirubin dispersed in gelatin. The different forms of bilirubin are selectively detected at two or more wavelengths.

While these elements represent advances in the art, improvement is desired for the determination of bilirubin. These elements are normally sold in a cartridge containing up to 50 individual elements. It has been observed that nonuniform results are sometimes obtained among elements due to sensitivity to environmental conditions when stored for a period of time, resulting in a bias because of a change in background color.

SUMMARY OF THE INVENTION

The problems described above have been solved with an analytical element for the determination of conjugated, unconjugated or total bilirubin comprising a support having thereon, in order,
  a substantially gelatin-free mordant layer comprising a positively-charged interactive mordant having at least one binding site for bilirubin, the mordant being dispersed in a hydrophilic binder material other than gelatin or its derivatives, the hydrophilic binder material being present in an amount of from about 2 to about 20 g/m$^2$,
  a radiation-blocking layer, and
  a porous spreading layer,
  provided that the element is free of colorimetric and fluorometric interactive compositions for bilirubin other than the mordant.

This invention also provides a method for the determination of conjugated, unconjugated or total bilirubin comprising the steps of:

A. contacting a sample of a liquid suspected of containing conjugated or unconjugated bilirubin with the analytical element described above, and B. measuring the amount of conjugated, unconjugated or total bilirubin bound to the interactive mordant.

The element of this invention can be used in an assay for either conjugated, unconjugated or total bilirubin, and is less susceptible to change resulting from environmental conditions (for example, high humidity and light). Hence, there is less variability from element to element in a given cartridge containing a multiplicity of elements immediately after manufacture and when stored for a period of time. It was surprising to find that gelatin was the source of the problem because gelatin is used as a binder in layers of many commercial analytical elements and was not previously known to cause such undesirable effects.

Upon discovery of the source of this problem, the gelatin in the mordant layer was substantially replaced with from about 2 to about 20 g/m$^2$ of a another hydrophilic binder material which did not cause the problem. A number of useful replacement binder materials are described in more detail below. The resulting improved element exhibits significantly less density change over time.

DETAILED DESCRIPTION OF THE INVENTION

The present invention relates to the determination of bilirubin (conjugated or unconjugated or the sum of both forms) in aqueous liquids. In particular, the invention can be used to assay biological fluids of either animals or humans, but preferably of humans. Such fluids include, but are not limited to, whole blood, plasma, serum, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

The method of this invention is practiced with a dry multilayer analytical element comprising a support having thereon a multiplicity of individual layers. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (for example, reflectance spectroscopy). Useful supports can be prepared from paper, metal foils, polystyrene, polyesters, polycarbonates, cellulose esters and other materials known in the art.

The outermost layer is a porous spreading layer prepared from any suitable fibrous or non-fibrous material or mixtures of either or both. The void volume and average pore size of this zone can be varied depending upon the fluid to be tested.

Useful spreading layers can be prepared using fibrous materials, either mixed with a suitable binder material or woven into a fabric, as described in U.S. Pat. No. 4,292,272 (issued Sept. 29, 1981 to Kitajima et al), polymeric compositions or particulate materials, for example, beads bound together with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication No. 57(1982)-101760. It is desirable that the spreading zone be isotropically porous, meaning that the porosity is the same in each direction in the zone as caused by interconnected spaces or pores between particles, fibers or polymeric strands.

The elements can have more than one spreading layer, each layer being prepared of the same or different materials and having the same or different porosity.

The element also comprises a radiation-blocking layer which contains a suitable radiation-blocking pigment, for example titanium dioxide or barium sulfate, distributed in a suitable hydrophilic binder material. Such binder materials include gelatin and its derivatives, polysaccharides, cellulosic derivatives, poly(vinyl alcohol), poly(vinyl pyrrolidone), acrylamide polymers and other known in the art. Preferably, this binder material is gelatin.

The interactive mordant needed to bind with bilirubin to provide a detectable product is located in a mordant layer located beneath the radiation-blocking layer. The interactive mordant and the hydrophilic binder material it is distributed in are described in more detail below.

Other layers, for example, subbing or filter layers, can be included in the element if desired. All of the layers in the element are generally in fluid contact with each other, meaning that fluids and nonmordanted reagents and reaction products can pass or be transported between superposed regions of adjacent layers.

The elements of the present invention are free of any interactive compositions which give a colorimetric or fluorometric response in the presence of bilirubin other than the interactive mordants described below. In particular, they are free of the diazonium salts and detectable ligands for forming detectable species known in the art for bilirubin determination, for example in U.S. Pat. Nos. 4,069,016 (issued Jan. 17, 1978 to Wu) and 4,548,905 (issued Oct. 22, 1985 to Wu).

The interactive mordants useful in the practice of this invention correspond to the mordants described in U.S. Pat. No. 4,069,017 (noted above) and the hydrophobic amines described in U.K. Patent Specification No. 2,085,581 (published Apr. 28, 1982) which are believed to become positively-charged mordants. In general, these mordants have one or more binding sites for bilirubin and comprise at least one moiety having a hydrophobic organic matrix and a charge-bearing cationic group. Such mordants can be monomeric or polymeric, but preferred mordant are homopolymers and copolymers having the properties noted above. They bind both conjugated and unconjugated forms of bilirubin.

Particularly useful interactive mordants are polymers having repeating units of the formula:

wherein A represents an organo group, Q represents a chemical bond or linking group, $M^+$ represents a quaternary ammonium or phosphonium group and $X^-$ represents an acid anion.

More particularly, A in the above structure represents a portion of a polymer backbone. As will be appreciated, A can be varied depending upon the particular polymeric backbone used. Especially good results, however, have been obtained when A represents an alkylene group. Generally, such alkylene groups contain from 2 to 10 carbon atoms. Copolymers useful as interactive mordants include those having from about 10 to about 90 weight percent of repeating units shown above and from about 10 to about 90 weight percent of additional repeating units which are non-interfering, that is, they do not chemically or physically interfere with bilirubin mordanting. Monomers which provide non-interfering units and that also impart hydrophobicity to the resulting copolymer include, but are not limited to, aliphatic and aromatic hydrocarbons (such as olefins and substituted olefins, styrene and substituted styrenes, alkylacrylates and alkylmethacrylates and derivatives thereof, and others known to one skilled in the art). Difunctional crosslinkable units can be incorporated into the copolymers if desired.

In the formula shown above, Q represents a chemical bond or a linking group which is generally a divalent hydrocarbon group, such as arylene, arylenealkylene, alkylenearylene, arylenebisalkylene, alkylenebisarylene, and others known to one skilled in the art. Preferably, Q is a group having from 5 to 10 carbon atoms.

$M^+$ represents a quaternary ammonium or phosphonium group having the same or different aryl, aralkyl or alkaryl groups each having up to 20 carbon atoms. Representative groups are well known to one skilled in the art. Preferably, $M^+$ is a quaternary ammonium group.

$X^-$ represents an acid anion, such as a halide ion (for example, chloride or bromide), nitrate, methosulfate, p-toluenesulfonate and others known to one skilled in the art.

Representative useful interactive mordants include:
poly(N,N,N-trimethyl-N-vinyl-benzylammonium chloride),
poly[styrene-co-benzyl(dimethyl)-p-vinyl-benzylammonium chloride],
poly(styrene-co-N-vinylbenzyl-N,N-dimethylammonium chloride-co-divinylbenzene),
poly(N,N,N-trimethyl-N-vinylbenzylammonium chloride-co-styrene),
poly(N,N,N-trioctyl-N-vinylbenzylphosphonium chloride) and
poly[styrene-co-(vinylbenzyl)-(trihexyl)ammonium chloride].

A further description of such interactive mordants including methods of preparing such materials is provided in U.S. Pat. No. 4,069,017, noted above, and incorporated herein by reference.

The mordant layer also contains a hydrophilic binder material which is permeable to bilirubin. As noted above, it is essential to the practice of this invention that this binder material not be gelatin or a derivative of gelatin. This binder material must also be non-interfering, that is, it does not interfere with the mordanting of bilirubin to the mordant described above. In other words, it should not be capable of binding or mordanting to bilirubin.

Useful binder materials can be identified readily with a simple test: coatings of the binder and mordant are subjected to two 15 watt cool white fluorescence tubes at a distance of 0.3 meter for 30 minutes followed by spectrophotometric measurements at 400 and 460 nm. These measurements are compared to similar measurements made prior to exposure to the tubes. A density difference of about 0.01 or more is unacceptable. All measurements are made at ambient temperature and humidity. Materials passing this test as binders include poly(vinyl alcohol), poly(N-vinyl 2-pyrrolidone), poly(N-vinyl 4-pyrrolidone), acrylamide homopolymers, copolymers of an acrylamide or methacrylamide and an N-vinyl pyrrolidone, carboxymethylcellulose and terpolymers of an N-vinyl pyrrolidone, a carboxy-containing vinyl monomer and an acrylamide or methacrylamide.

Particularly useful binders include copolymers of an acrylamide or methacrylamide (for example, acrylamide, methacrylamide, N-isopropyl acrylamide and others known in the art) and an N-vinyl pyrrolidone (such as N-vinyl 2-pyrrolidone and N-vinyl 4-pyrrolidone), and terpolymers of an N-vinyl pyrrolidone (as defined above), a carboxy-containing vinyl monomer (such as acrylic acid, methacrylic acid, itaconic acid, others known in the art and their functional equivalents, for example anhydrides and esters) and an acrylamide or methacrylamide (as defined above). Suitable molar ratios of the monomers used to prepare these polymers are within the skill of ordinary workers in the art. Poly(acrylamide-co-N-vinyl-2-pyrrolidone) is a preferred hydrophilic binder material for use in the mordant layer in the practice of this invention.

The amount of interactive mordant used in the element can be varied depending upon the particular range of bilirubin content over which a specific bilirubin assay is designed to be useful. Details regarding useful amounts are provided in U.S. Pat. No. 4,069,017, noted above.

The amount of hydrophilic binder material in the mordant layer should be sufficient to adequately disperse the mordant therein and to form a suitable film. The amount will also depend upon whether a monomeric or polymeric mordant is used. Where the mordant is a film-forming polymer, less binder material may be needed. Generally, the amount of binder is from about 2 to about 20 $g/m^2$ with amount of from about 5 to about 20 $g/m^2$ being preferred.

Other optional addenda (including buffers, surfactants and the like) can be added to one or more layers of the element, if desired. Also useful in the element are one or more bilirubin effectors or promoters as they are also known in the art. Such materials include sodium benzoate, caffeine, gum arabic, salicylate, bile salts and mixtures thereof. Preferably, such materials are included in the porous spreading layer of the elements.

A variety of different elements, depending on the method of assay, can be prepared in accordance with the present invention. Elements can be configured in a variety of forms, including elongated tapes of any desired width, sheets, slides or chips. Generally, the elements are individual slides which are packaged together in cartridges for use in automated analyzers.

The assay of this invention can be manual or automated. In general, in using the dry elements, total bilirubin determination (that is, measurement of all forms) is made by taking the element from a supply roll, chip packet or other source and physically contacting it with a sample (for example, up to 200 $\mu l$) of the liquid to be tested so that the sample and reagents (that is, the interactive mordant) within the element become mixed. Such contact can be accomplished in any suitable manner, for example, by dipping or immersing the element into the sample or, preferably, by spotting the element by hand or machine with a drop of the sample with a suitable dispensing means.

After sample application, the element can be exposed to conditioning, such as incubation, heating or the like, that may be desirable to quicken or otherwise facilitate obtaining any test result.

When the mordant binds to bilirubin, a detectable change results which is readily measured using suitable apparatus for reflection spectrophotometry. Such apparatus is well known in the art. The signal from the detectable species so measured is indicative of the amount of total bilirubin in the fluid tested.

Alternatively, the method and element of this invention can be used to measured either conjugated or unconjugated forms of bilirubin according to the teaching of U.S. Pat. No. 4,338,095, noted above, and which is incorporated herein by reference. Generally, this selective measurement of one or both forms of bilirubin is accomplished by contact of sample and element as described above, and by measuring the absorption or emission spectra at two or more wavelengths and performing the appropriate calculations.

In the example which follows, illustrating the practice of this invention, the materials used were obtained as follows:

TRITON X-405 nonionic surfactant from Rohm and Haas (Philadelphia, Pa.),

BRIJ 78 surfactant from Ruger (Irvingtion, N.J.),

SURFACTANT 10G surfactant from Olin Corporation (Stamford, Conn.), and the remainder either from Eastman Kodak Company (Rochester, N.Y.) or prepared using standard procedures and readily available starting materials.

EXAMPLE

Comparison of Elements with Different Binder Materials in Mordant Layer

This is a comparison of the element of the present invention to a Control element like that described in U.S. Pat. No. 4,069,017, noted above, and which has been available commercially for some time.

The element of this invention had the format and components illustrated as follows:

| Spreading Layer | Titanium dioxide | 25–125 g/m² |
| --- | --- | --- |
| | Cellulose acetate | 4–20 g/m² |
| | TRITON X-405 surfactant | 0.5–5 g/m² |
| | BRIJ 78 surfactant | 0.5–2.5 g/m² |
| | Caffeine | 1–10 g/m² |
| | Sodium benzoate | 1–10 g/m² |
| Subbing Layer | Poly(N—isopropyl-acrylamide) | 0.1–2 g/m² |
| Radiation-Blocking Layer | Titanium dioxide | 5–50 g/m² |
| | Gelatin | 0.5–5 g/m² |
| | SURFACTANT 10G surfactant | 0.05–1 g/m² |
| | DAXAD-30 surfactant | 0.05–1 g/m² |
| Mordant Layer | Poly(acrylamide-co-N—vinyl 2-pyrrolidone) | 2–20 g/m² |
| | Poly(styrene-co-N—vinylbenzyl-N,N—dimethylammonium chloride-co-divinylbenzene) | 0.2–2.5 g/m² |
| | N,N—bis(2-hydroxyethyl)-glycine (bicine) | 1–10 g/m² |
| | Potassium chloride | 0.05–1 g/m² |
| | SURFACTANT 10G surfactant | 0.05–1 g/m² |
| | Poly(ethylene terephthalate) Support | |

The element of this invention contains poly(acrylamide-co-N-vinyl 2-pyrrolidone) as the binder material in the mordant layer. A Control element was similarly constructed except that it contained gelatin as the mordant layer binder material.

Both elements were tested in the following manner. Cartridges of each of the Control and invention elements (50 elements in each cartridge) were subjected to 21° C. and 50% relative humidity for various periods of time ranging up to ten days after manufacture. One cartridge of each type of element was tested immediately after manufacture. All 50 elements of each cartridge were then tested for bilirubin determination using test fluids containing moderate amounts of bilirubin (conjugated and unconjugated forms) and an EKTACHEM 700 Clinical Chemistry analyzer (available from Eastman Kodak Co., Rochester, N.Y.).

The results of these tests, that is, predicted concentration as a function of storage time. The average determinations of all 50 elements in a given cartridge. The elements of the present invention showed very little change in predicted conjugated and unconjugated bilirubin ($B_c$ and $B_u$) concentration when exposed to 21° C. and 50% relative humidity for up to 10 days. However, the Control elements showed significant variability under these conditions. Therefore, the present invention exhibits unexpected improvement over the Control element which is taught by U.S. Pat. No. 4,069,017, noted above.

Table I below summarizes the data, and also provides the values for the sum of $B_u$ and $B_c$.

TABLE I

| Days of Keeping 21° C., 50% R.H. | Control (mg/dl) | | | Invention (mg/dl) | | |
| --- | --- | --- | --- | --- | --- | --- |
| | $B_u$ | $B_c$ | $B_u + B_c$ | $B_u$ | $B_c$ | $B_u + B_c$ |
| 0* | 1.85 | 2.39 | 4.24 | 1.97 | 2.18 | 4.15 |
| 3 | 1.92 | 2.32 | 4.24 | 2.01 | 2.21 | 4.22 |
| 5 | 2.00 | 2.15 | 4.15 | 2.01 | 2.21 | 4.22 |
| 7 | 2.01 | 2.12 | 4.13 | 2.02 | 2.19 | 4.21 |
| 10 | 2.05 | 2.04 | 4.09 | 2.01 | 2.21 | 4.22 |

*Tested right after manufacture.

The invention has been described in detail with particular reference to preferred embodiments thereof, but it will be understood that variations and modifications can be effected within the spirit and scope of the invention.

We claim:

1. A method for the determination of conjugated, unconjugated or total bilirubin comprising the steps of:
   A. contacting a sample of a liquid suspected of containing conjugated or unconjugated bilirubin with an analytical element comprising a support having thereon, in order,
      a gelatin-free mordant layer comprising a positively-charged interactive mordant having at least one binding site for bilirubin, said mordant being dispersed in a hydrophilic binder material other than gelatin or its derivatives, said hydrophilic binder material being present in an amount of from about 2 to about 20 g/m², and being selected from the group consisting of copolymers of acrylamide or methacrylamide and N-vinyl pyrrolidone and terpolymers of an N-vinyl pyrrolidone, a carboxy-containing vinyl monomer and an acrylamide or methacrylamide,
      a radiation-blocking layer, and
      a porous spreading layer,
      provided that said element is free of colorimetric and fluorometric interactive compositions for bilirubin other than said mordant, and
   B. measuring the amount of conjugated or unconjugated or total bilirubin bound to said interactive mordant.

2. The method of claim 1 wherein total bilirubin is determined.

3. The method of claim 1 wherein either or both conjugated or unconjugated bilirubin is determined by spectrophotometric measurements at more than one wavelength.

4. An analytical element for the determination of conjugated, unconjugated or total bilirubin comprising a support having thereon, in order,
   a substantially gelatin-free mordant layer comprising a positively-charged interactive mordant having at least one binding site for bilirubin, said mordant being dispersed in a hydrophilic binder material other than gelatin or its derivatives, said hydrophilic binder material being present in an amount of from about 2 to about 20 g/m², and being selected from the group consisting of copolymers of acrylamide or methacrylamide and N-vinyl pyrrolidone and terpolymers of an N-vinyl pyrrolidone, a carboxy-containing vinyl monomer and an acrylamide or methacrylamide,
a radiation-blocking layer, and
a porous spreading layer,
provided that said element is free of colorimetric and fluorometric interactive compositions for bilirubin other than said mordant.

5. The element of claim 4 wherein said binder material is a copolymer of acrylamide and N-vinyl 2-pyrrolidone.

6. The element of claim 4 wherein said interactive mordant is selected from the group consisting of poly(N,N,N-trimethyl-N-vinyl-benzylammonium chloride), poly[styrene-co-benzyl(dimethyl)p-vinyl-benzylammonium chloride], poly(styrene-co-N-vinylbenzyl-N,N-dimethylammonium chloride-co-divinylbenzene), poly(N,N,N-trimethyl-N-vinylbenzylammonium chloride-co-styrene), poly(N,N,N-trioctyl-N-vinylbenzylphosphonium chloride) and poly[styrene-co-(vinylbenzyl)-(trihexyl)ammonium chloride].

7. The element of claim 4 wherein said spreading layer contains a bilirubin effector.

8. The element of claim 4 wherein said radiation-blocking layer comprises inorganic pigment particles dispersed in a second hydrophilic binder material.

9. The element of claim 4 wherein said interactive mordant is a polymer having repeating units of the formula:

wherein A represents an organo group, Q represents a quaternary ammonium or phosphonium group and $X^-$ represents an acid anion.

10. The element of claim 9 wherein $M^+$ represents a quaternary ammonium group.

11. An analytical element for the determination of conjugated, unconjugated or total bilirubin comprising a nonporous support having thereon, in order,
a substantially gelatin-free mordant layer comprising a positively-charged, polymeric interactive mordant having at least one binding site for bilirubin and having recurring units represented by the formula

wherein A represents an organo group, Q represents a chemical bond or linking group, $M^+$ represents a quaternary ammonium or phosphonium group and $X^-$ represents an acid anion, said mordant being dispersed in a first hydrophilic binder material other than gelatin or its derivatives, said first hydrophilic binder material being present in an amount of from about 2 to about 20 $g/m^2$, and being selected from the group consisting of copolymers of acrylamide or methacrylamide and N-vinyl pyrrolidone and terpolymers of an N-vinyl pyrrolidone, a carboxy-containing vinyl monomer and an acrylamide or methacrylamide,
a radiation-blocking layer comprising an inorganic pigment dispersed in a second hydrophilic binder material, and
a porous blushed polymer spreading layer,
provided that said element is free of colorimetric and fluorometric interactive compositions for bilirubin other than said mordant.

12. The element of claim 11 wherein said second hydrophilic binder material is gelatin.

13. The element of claim 11 wherein said first hydrophilic binder material is poly(acrylamide-co-N-vinyl-2-pyrrolidone) and said mordant is poly(styrene-co-N-vinylbenzyl-N,N-dimethylammonium chloride-co-divinylbenzene).

* * * * *

UNITED STATES PATENT AND TRADEMARK OFFICE
CERTIFICATE OF CORRECTION

PATENT NO. : 4,788,153

DATED : November 29, 1988

INVENTOR(S) : Richard L. Detwiler et al.

It is certified that error appears in the above-identified patent and that said Letters Patent is hereby corrected as shown below:

Column 9, lines 36-37, the part reading "Q represents a quaternary ammonium" should read -- Q represents a chemical bond or linking group, $M^+$ represents a quaternary ammonium --.

Signed and Sealed this

Twenty-fourth Day of October, 1989

Attest:

DONALD J. QUIGG

*Attesting Officer*  *Commissioner of Patents and Trademarks*